United States Patent [19]

Panek

[11] Patent Number: 4,643,891
[45] Date of Patent: * Feb. 17, 1987

[54] PREPARATION AND USE OF A $^{195m}$AU-CONTAINING LIQUID

[75] Inventor: Karel J. Panek, Heilo, Netherlands

[73] Assignee: Mallinckrodt Diagnostica (Holland) B.V., Netherlands

[ * ] Notice: The portion of the term of this patent subsequent to Nov. 8, 2000 has been disclaimed.

[21] Appl. No.: 542,171

[22] Filed: Oct. 14, 1983

Related U.S. Application Data

[63] Continuation-in-part of Ser. No. 140,781, Apr. 16, 1980, Pat. No. 4,414,145.

[51] Int. Cl.$^4$ .................. A61K 43/00; A61N 5/12; C09K 11/00; C09K 11/04
[52] U.S. Cl. .................. 424/1.1; 128/654; 128/659; 128/668; 250/432 PD; 252/645; 423/25; 423/99; 423/100
[58] Field of Search .................. 252/645; 250/432 PD; 424/1.1; 423/25, 99, 100, 2; 128/654, 659, 668

[56] References Cited

U.S. PATENT DOCUMENTS

| | | | |
|---|---|---|---|
| 3,317,312 | 5/1967 | Kraus et al. | 423/25 |
| 3,785,990 | 1/1974 | Benjamins et al. | 250/432 PD |
| 3,898,044 | 8/1975 | Strecker et al. | 252/301.1 R |
| 3,935,098 | 1/1976 | Oda et al. | 423/25 |
| 4,414,145 | 11/1983 | Panek | 252/645 |

OTHER PUBLICATIONS

Lebowitz et al., "Radionuclide Generator Systems", Sem. in Nucl. Med., vol. 4, No. 3 (Jul.) 1974, pp. 257–268.
Gupta, et al., "Ion Exchange Behavior of Mercury (II) . . . ", Nuclear Science Abstracts, vol. 27, Abs. #11668 (1973).
Halasz, et al., "Microbeads Coated with a Porous Thin Layer . . . ", Analytical Chem., 36(7), 1964, pp. 1178–1186.
Christensen et al., "Ion Binding by Synthetic Macrocyclic Compounds", Science, vol. 174, No. 4008 (Oct. 1971), pp. 459–467.

Primary Examiner—Stephen J. Lechert, Jr.
Assistant Examiner—Howard J. Locker
Attorney, Agent, or Firm—Bernard, Rothwell & Brown

[57] ABSTRACT

A method for preparing a $^{195m}$Au-containing liquid is provided. In the method, $^{195m}$Hg is adsorbed on an adsorption agent and then the daughter radioisotope $^{195m}$Au is eluted from the adsorption agent with an eluant containing a gold-complexing agent. The adsorption agent comprises a mercury ion-binding material having a substantially stronger adsorption affinity for mercury ions than for gold ions.

Also disclosed are a radioisotope generator capable of producing a $^{195m}$Au-containing liquid and a process for conducting a radiodiagnostic examination on a warm-blooded animal using a $^{195m}$Au-containing liquid.

13 Claims, 4 Drawing Figures

PREPARATION AND USE OF A $^{195m}$AU-CONTAINING LIQUID

This application is a continuation-in-part of Ser. No. 140,781, filed Apr. 16, 1980, now U.S. Pat. No. 4,414,145.

The present application relates generally to a method for preparing a $^{195m}$Au-containing liquid comprising adsorbing $^{195m}$Hg on an adsorption agent and then eluting the daughter radioistope $^{195m}$Au from the adsorption agent. The present invention also relates to a method for conducting a radiodiagnostic examination using a $^{195m}$Au-containing liquid and to a radioisotope generator capable of producing a $^{195m}$Au-containing liquid.

Radioisotopes are frequently employed in medicine for diagnostic purposes. One radioisotope frequently used for diagnostic purposes such as diagnostic examinations is $^{99m}$Tc, generally in the form of pertechnetate. $^{99m}$Tc is a useful radioisotope for diagnostic examinations because it emits gamma rays of a suitable energy level and in sufficient quantity that commonly used detection systems such as gamma cameras can be used with maximum efficiency.

However, for certain applications, the comparatively long half-life of $^{99m}$Tc, about six hours, is advantageous since the radioactive $^{99m}$Tc material remains circulating in the body for a relatively long period of time. Consequently, an immediate repetition of a particular diagnostic examination is not possible. Moreover, the relatively long half-life of $^{99m}$Tc has an adverse influence on the radiation load, i.e., the overall quantity of radiation to which a patient undergoing diagnosis is exposed is comparatively large.

In particular, $^{99m}$Tc is less than suitable for cardiological examinations due to its relatively long half-life. For example, a radioisotope having a relatively short half-life is required to evaluate the movement of the ventricle walls of the heart and to perform quantitative measurements of heart functions such as ejection fraction computations and determination of the size of shunts.

Therefore, a radioisotope having a half-life between, for example, about 4 and 45 seconds would consequently be of great importance in radiodiagnostic examinations, particularly in cardiological examinations. Of course, a radioisotope having such a short half-life could not be transported any significant distance and would therefore have to be produced at approximately the same location where it is to be used. It is, therefore, apparent that stringent requirements must be imposed upon the mode of preparation of such a radioisotope, since only a very simple and hence rapid preparation, preferably from an isotope generator, can be conducted in a hospital or clinical laboratory to effectively produce such a radioisotope having a relatively short half-life with a minimum of radiation complications.

Of the many possible radioisotopes, the radioisotope $^{195m}$Au would apparently be very suitable for the above-mentioned purposes since $^{195m}$Au emits only gamma rays, the emitted rays are of a suitable energy (about 261 KeV), and the rays are emitted in a sufficient quantity to enable observation with a suitable detection apparatus such as a gamma camera. Furthermore, the half-life of $^{195m}$Au is only about 30.6 sec.

The $^{195m}$Au radioisotope is formed as a decay product from the parent isotope $^{195m}$Hg having a half-life of about 40 hours which is of sufficient duration for practical use. The parent isotope can be produced in a cyclotron by irradiating $^{197}$Au with protons and then isolating the parent isotope from the exposed material.

Y. Yano (Radiopharmaceuticals, Ed. Subramanian et al., Soc. Nucl.-Medic. Inc., N.Y. 1975, pp 236-245) stated that the generation of $^{195m}$Au from $^{195m}$Hg was under investigation and that a separation of the parent isotope and the daughter radioisotope by means of an ion exchanger was being studied. However, in the meantime, no publication has reported that anyone has succeeded in satisfactorily obtaining this radioisotope which appears well adapted for certain radiodiagnostic examinations.

Furthermore, the above-mentioned literature article suggested the use of an ion exchanger in the separation of the $^{195m}$Hg parent isotope from the $^{195m}$Au radioisotope. An ion exchanger is usually understood to be a resin, for example, a sulphonated phenolformaldehyde resin or a phenol-formaldehyde resin provided with other functional groups. However, these resins or copolymerisates would be less than suitable to serve as an adsorption agent for the $^{195m}$Hg parent isotope because their adsorptivity for mercury ions usually does not differ significantly from that for gold ions and, in addition, their radiation stability is usually rather low. Furthermore, these resins often contain monomers or other low-molecular weight compounds which can contaminate the eluate upon elution of the daughter isotope. Due to the relative short half-life of the daughter isotope, any purification of the eluate is practically impossible.

In accordance with one aspect of the present invention, a method is provided for preparing a $^{195m}$Au containing liquid in a simple and efficient manner by adsorbing $^{195m}$Hg on a suitable adsorption agent and subsequently eluting the daughter isotope $^{195m}$Au from the adsorption agent with a suitable eluant, the adsorption agent comprising a mercury-ion binding material having a greater adsorption affinity for mercury ions than for gold ions. In another aspect of the present invention, a radioisotope generator capable of producing a $^{195m}$Au-containing liquid is provided, the generator including an adsorption agent comprising a mercury-ion binding material having a stronger adsorption affinity for mercury ions than for gold ions.

The method for preparing a $^{195m}$Au-containing liquid and the radioisotope generator capable of producing a $^{195m}$Au-containing liquid in accordance with the present invention preferably are used in conjunction with processes for conducting radiodiagnostic examinations in warm-blooded animals such as a human, particularly in examinations of the heart of the animal. Other potential uses for the $^{195m}$Au-containing liquid are in studies of peripheral arterial blood supply such as renal artery flow studies, cereberal arterial flow studies and the like. Thus, in a further aspect of the present invention, a process for conducting a radiodiagnostic examination using a $^{195m}$Au-containing liquid is provided, the process comprising administering to an animal the $^{195m}$Au-containing liquid and monitoring the radioactivity emitted from the animal in a desired location such as the heart or portion thereof.

Figure 1:
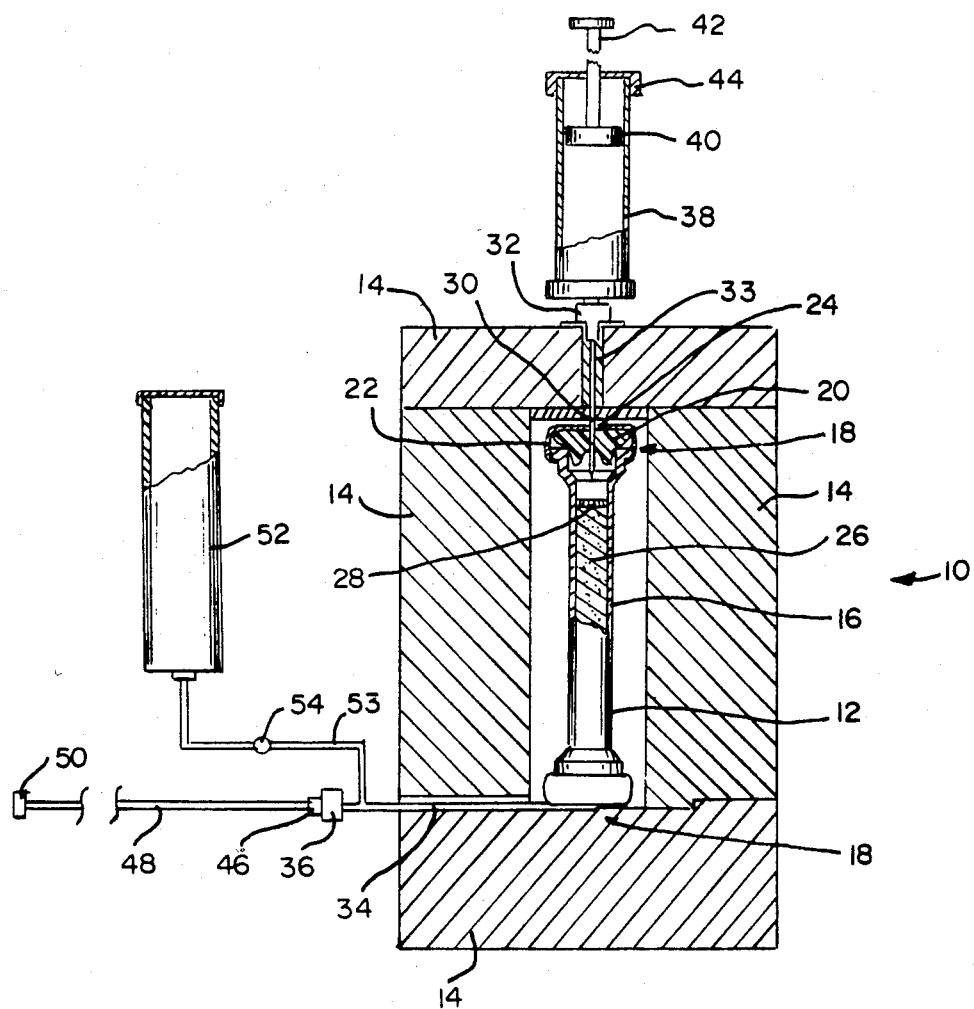
FIG. 1 is a cross-sectional view of a radioisotope generator particularly adapted for the generation of a $^{195m}$Au-containing liquid and FIG. 2 illustrates the type of data which may be obtained upon administration of a $^{195m}$Au-containing liquid to an animal.

As was mentioned above, the method of preparation and generator of the present invention utilize an adsorption agent comprising a mercury ion-binding material characterized as having a stronger adsorption affinity for mercury ions than for gold ions. This characteristic of the adsorption agent can be provided by a wide variety of mercury ion-binding materials contained within the adsorption agent. Suitable mercury ion-binding materials may be organic or inorganic and include activated carbon, silver, hydrated manganese dioxide, sulphides of metals having an atomic weight of at least 25 such as zinc sulphide, iron sulphide, manganese sulphide, zirconium sulphide and silver sulphide and mercury complexing or chelating compounds such as those containing thio-, amino-, hydroxy, carbamate, dithiocarbamate, xanthate or carboxy functions in a terminal or final position, i.e., as a terminal functional group for the compound.

While all of the above mercury ion-binding materials function satisfactorily in providing the adsorption agent with a stronger adsorption affinity for mercury ions than gold ions, some of the materials, when used alone, may be deficient in other characteristics such as mechanical and flow properties which are desirable to enable the adsorption agent to efficiently adsorb $^{195m}$Hg and to allow elution of $^{195m}$Au.

For example, some of the above mentioned mercury ion-binding materials such as silver, hydrated manganese dioxide and metal sulfides have an adsorptivity which, in suitable circumstances, provides an excellent separation between mercury and gold ions, but their normal structure and mechanical properties such as packing flow characteristics may be insufficient for the efficient production of an $^{195m}$Au-containing liquid from adsorbed $^{195m}$Hg when these materials are used as the sole adsorption agent.

Consequently, it is preferable that the mercury ion-binding material of the adsorption agent be utilized in conjunction with a suitable substrate material. The mercury ion-binding material may be combined with the substrate material, e.g., as a physical mixture such as a mixture of finely divided solids, as a filler within the substrate material, as a surface coating on the substrate material, or may be chemically bonded to the substrate material. Preferably, although not necessarily, the substrate material is generally capable of contributing to the adsorption of mercury ions and to the separation of mercury ions and gold ions. Activated carbon is one example of a substrate material which is capable of contributing to the adsorption of mercury ions and to the separation of mercury ions and gold ions since this material acts as a mercury ion-binding material. Other suitable substrate materials may be selected from a wide variety of normally solid substantially organic and inorganic materials which have the necessary non-toxicity, chemical and radiation stability, and mechanical properties providing good packing and flow characteristics for liquids passing therethrough. Generally, such substrate materials are particulate and preferably are finely divided. Although the size of the particles of substrate material may vary considerably, preferably the particles are in the range of about 0.005 to about 1.0 mm. The same criteria apply when the mercury ion binding material is the sole component of the adsorption agent. Suitable substrate materials for use in adsorption agents include silica gel, aluminum oxide, natural or synthetic substances which contain silicates such as aluminum silicate as the primary constituent, and activated carbon. Generally, these substrate materials can be characterized as porous type substrate materials. Other suitable substrate materials include commercially available chromotographic packing materials which may be irregularly or spherically shaped such as totally or superficially porous controlled pore glass beads as well as non porous solid glass beads, capillaries or other suitably shaped glass objects. Furthermore, suitable organic substrate materials include natural or synthetic polymers or copolymers such as styrene or copolymers thereof which are shaped to a suitable form and size such as resin beads and spherical or irregular granules in either porous or solid form. Silica gel, porous glass beads and solid glass beads are particularly preferred substrate materials for the purposes of the present invention.

The adsorption agent, whether consisting of one or more mercury ion-binding materials alone or in combination with a substrate material, should preferably be stable against radiation and of sufficient chemical stability that little or no contamination of the eluate is realized upon elution of the adsorption agent. This preference is based on the fact that the daughter radioisotope, due to its relatively short half-life, must by necessity be administered directly to a patient and thus cannot be purified before administration. Adsorption agents which are substantially or completely inorganic in nature are preferred adsorption agents for the $^{195m}$Hg parent isotope since the assurance that the adsorption agent is stable against radiation and does not contaminate the eluate is generally greater with inorganic materials than with organic materials even though a number of known synthetic polymers or copolymers such as styrene are relatively stable against radiation and can be obtained in a relatively pure form.

As was stated previously, the mercury ion-binding material and substrate material can be combined in various manners. One suitable method is to subject particles of the substrate material to a surface treatment so that the particles are provided with a mercury ion-binding material at their surface or inside their pores. Preferred mercury ion-binding materials for this method include hydrated manganese dioxide, silver, and metal sulphides such as zinc sulphide, zirconium sulphide, cadmium sulphide or silver sulphide, particularly when the substrate material is silica gel or glass beads. The above-mentioned method for treating the substrate material can be used in the treatment of inorganic substrate materials as well as for organic substrate materials such as styrene resins.

The amount of mercury ion-binding material relative to the substrate material in the adsorption agent is not critical but of course sufficient mercury ion binding material should be included so that a sufficient amount of mercury ions can be adsorbed. For example, when silica gel is treated with zinc sulphide as the mercury ion binding material, the silica gel may include about 0.1–20 mg, preferably about 0.8–10 mg, of zinc sulphide per gram of silica gel. Other mercury ion-binding materials can be combined with substrate materials such as silica gel in approximately the same molar proportions as zinc sulphide to produce satisfactory adsorption agents. Generally, the amount of mercury ion-binding material included in the adsorption agent should be sufficient to adsorb at least about 10 mCi, preferably at least about 20 mCi, of $^{195m}$Hg per g of adsorption agent.

Another very suitable method of treating a substrate material is to subject the particles of the material to a surface treatment with an organic compound which, due to a chemical reaction, is bonded or anchored to the surface of the particles. Such compounds for the surface treatment preferably contain various types of functional groups, preferbly (a) an anchor group capable of reacting with the surface of the particles of substrate material, (b) a spacer group which produces a distance from the surface of the particles, and (c) one or more terminal groups which provide the adsorption agent with a greater affinity for mercury ions than for gold ions. Preferably, the terminal groups of the compounds are a complex-forming ligand. In the treatment of the substrate material with the compound, the anchor group of the compound forms covalent bonds with the surface of the particles in a chemical reaction which thereby binds the compound to the surface of the particles of substrate material.

Chemically bonded or anchored groups may have thiol,-amino-, hydroxy, carbamate-, dithiocarbamate-, xanthate, or carboxy terminal functional groups as complex-forming ligands, these groups having a stronger adsorption affinity for mercury ions than for gold ions, and such functional groups may be used alone or in combination with each other with a particular substrate material. In general, the number and configuration of the terminal functional groups of a compound will determine the capability of a treated substrate material to adsorb mercury ions in preference to gold ions.

Other complex-forming ligands suitable to bind mercury ions in and adsorption agent are macrocyclic or heteromacrocyclic ligands which may be anchored to the surface of a substrate material either directly or via a spacer group. Such anchored macrocyclic ligands, with rings of the proper size to fit the dimensions of the mercury ions to be adsorbed, may have a single ring, preferably in one plane, to form a complex with mercury, or two or more planar rings to form complexes of the sandwich type, or they may be polycyclic ligands which form complexes in which mercury ion is completely encapsulated. Examples of such suitable macrocyclic, heteromacrocyclic or polycyclic ligands, namely those with 14-18 member rings containing one or more O-, S-, and/or N-atoms, are, for instance, cyclic polyethers, polyamines, polythioethers or mixed donor macrocycles such as those described, for example, by Christensen et al. in *Science* 174, 459 (1971) or in *Chem. Reviews* 74, 351 (1974).

Some of the above-mentioned adsorption agents with an anchored terminal complex-forming ligand such as, for instance, controlled pore glass (CPG) with anchored aminopropyl groups, CPG with thiol groups, CPG with dihydrolipoamide groups, and some others are already commercially available. Those adsorption agents not readily obtainable or "tailored" adsorption agents may be prepared in several ways as, for instance, in the manners described by Unger, "Chemical Surface Modification of Porous Silica Adsorbents in Chromatography," *Merck Kontakte*:2, 32 (1979) and by Leyden and Luttrell, "Preconcentration of Trace Metals Using Chelating Groups Immobilized via Silylation," *Anal. Chem.*: 47 1612 (1975). Thus, for example, an adsorption agent including a silica gel, silicate or CPG substrate material with anchored thiol- or amino-terminal functional groups can be prepared by treating silica gel, silicate or glass particles with a silane containing mercaptoalkyl- or aminoalkyl- groups, for instance, by treating the particles with a silane compound such as an alkoxysilane or chlorosilane and then converting the silanol≡Si—OH groups on the surface of the treated particles to a ≡Si—O—Si—R chain, R being a mercaptoalkyl group or a 3-(2-aminoethylamino)propyl group, which is firmly bonded to the surface of the particles by a —Si—spacer group.

Although nonporous substrate materials with a high silica content, for instance solid glass beads, can be treated in the same manner as described above to obtain an adsorption agent containing anchored complex-forming ligands, the generally small surface of such solid particles has only a relatively low concentration of reactive silanol groups. Therefore, after the above described treatment, a product is obtained which contains a smaller number of anchored complex-forming ligands per surface area unit. As a consequence, it may be more difficult to prepare a product with an adsorption capacity (the adsorption capacity being proportional to the number of available ligands) sufficient to make a suitable adsorption agent, particularly when weightable amounts of metals, like mercury, should be retained on the adsorption agent.

To prepare a suitable adsorption agent from such solid bodies such as glass beads and the like, alternative techniques such as those known generally as thin film coating techniques can be successfuly employed. Because these techniques are based on physical adherence between a film and the surface of the coated particle rather than on chemical reaction between the film and the particle, thin film techniques can be used for all types of solid bodies irrespectively of their origin, nature or composition including, for instance, granulated organic polymers or copolymers, resin beads and the like as well as the other substrate materials mentioned previously.

Numerous examples of such thin film coating techniques are known including vacuum evaporation techniques, particularly reactive sputtering such as that described by Perny Guy, *Thin Solid Films* 6/3 R-25-28 (1970) for coating with thin films of metal sulphides. An alternative technique for deposition of thin layers of a desired substance on solid bodies such as glass beads is the technique described by Halasz et al, *Anal. Chem.* 36, 1178-1186 (1964). This latter technique, which is very simple, has a further advantage in that a thin layer on solid surfaces can be produced from materials which cannot be easily evaporated or evaporated without changes in their structure such as by decomposition and the like. By working with the substances to be deposited either in the form of dry powders or in the form of powders suspended or slurried in a suitable solvent, with or without the presence of binding material, this technique is particularly suitable for the coating of solid bodies with thin layers of not only simple adsorbing substance such as, for instance, metal sulphides, hydrated metal oxides, metals and the like, but it is also particularly suitable for producing thin layers from organic compounds including those compounds containing one or more complex-forming ligands.

A further advantage of the latter technique is that it is possible to coat solid bodies with composite thin layers, that is, thin layers comprising two or more substances or compounds which differ in nature or properties. Thus, for instance, this technique allows the deposition of not only a single, chemically well-defined substance such as a metal sulphide or hydrated oxide, but also the deposition of mixtures of various substances in various proportions. Consequently, solid bodies can be provided with thin layers of, for example, a combination of several metal sulphides, a combination of metal sulphides with, for instance, metal oxides, hydrated oxides, hydroxides and the like. Similarly, it is possible to combine inorganic materials with organic substances or a variety of purely organic substances including those containing one or more complex-forming ligands. Therefore, this technique offers an enormous number of possible variations to produce the desired adsorption agent, that is, an adsorption agent having stronger adsorption for mercury ions than for gold ions.

Yet another method for producing solid bodies coated with thin films which is particularly simple to carry out exploits a slow precipitation reaction that results in a slow deposition of a minutely soluble or insoluble reaction product on the solid surfaces which are in direct contact with the reaction mixture. This method, particularly suitable for deposition of thin films of inorganic substances such as metal sulphides, hydrated oxides, hydroxides and the like, can be conducted in a similar fashion to the method described, for instance, by Betenekov et al., *Radiokhimiya* 20/3, 431–438 (1978).

For deposition of thin films of, for instance, metal sulphides, the above method may employ organic sulphur-containing compounds which, when dissolved in a solution, can slowly decompose under specific conditions and thus be a source for slowly releasing sulphur, SH radicals or hydrogen sulphide to react with an appropriate metal present in the same solution. This method thereby results in a slow deposition of the particular insoluble metal sulphide in the form of an adherent thin layer on solid bodies such as for instance glass beads which are present or suspended in the same solution to thereby produce the desired adsorption agent.

As was stated previously, the method of the present invention for preparing a $^{195m}$Au-containing liquid includes the step of adsorbing the $^{195m}$Hg parent isotope on an adsorption agent. The parent isotope $^{195m}$Hg can be produced in known manner from $^{197}$Au by irradiating $^{197}$Au with protons in a cyclotron. Essentially pure $^{195m}$Hg can be isolated from the irradiated material in a likewise known manner, for example, by dry distillation.

The adsorption of $^{195m}$Hg on the adsorption agent can be achieved by contacting the adsorption agent with a solution containing $^{195m}$Hg ions and having a pH of about 1–10, preferably of about 5–6. Such a solution can be obtained by dissolving $^{195m}$Hg in concentrated acid, for example, nitric acid, diluting the resulting solution with water, and then bringing the solution to a pH of about 1–10, preferably to a pH of about 5–6. By contacting the adsorption agent with the $^{195m}$Hg ion-containing solution thus obtained, the $^{195m}$Hg-ions are adsorbed and adsorption agent is thereby charged with radioactivity, i.e., radioactive $^{195m}$Hg from which the daughter radioisotope $^{195m}$Au is continuously formed by the process of natural decay. The formed daughter radioisotope can be separated from the adsorption agent loaded with $^{195m}$Hg by a process known as elution, i.e., by washing the adsorption agent with a suitable liquid in which the daughter radioisotope appears in essentially pure form without substantial contamination with the parent isotope $^{195m}$Hg. Depending upon the particular adsorption agent utilized, generally the capacity of the adsorption agent for mercury is in the range of about 1 to about 50 mg per gram of adsorption agent.

For the elution of the daughter radioisotope $^{195m}$Au from the charged adsorption agent, a solution of gold ion-complexing agent can be used. Gold ions can be eluted in good yields by using solutions containing an amine, an amino acid, or a sulphur-containing compound such as an organic mercapto compound as the gold ion-complexing agent. Preferred gold ion-complexing agents include thiosulphate, tris(hydroxymethyl)aminomethane, hippurate, glutathione, mercaptopropionyl glycine, thiomalate, thiosalicylate or rhodanide. If desired, a minor amount, e.g. about 0.00001 to about 0.0001 molar, of non-radioactive gold, a so-called gold carrier, may also be present in the eluant solution.

Due to the relative short half-life of $^{195m}$Au, it is necessary to use the obtained eluate as soon as possible, for example, by immediately administering the eluate to the body of a patient. Therefore, a pharmaceutically-acceptable solution of the gold-ion complexing agent must be generally used as the eluant.

While it is preferred that the eluant used for eluting the adsorption agent be aqueous, other solvents may be used in formulating the solution of gold-complexing agent as long as they are not harmful to the animal to which the eluate is to be administered. The amount of gold-complexing agent in the eluant is not believed to be critical so long as the eluant is capable of eluting sufficient $^{195m}$Au for the intended purpose, but preferably the eluant contains about 0.0001 to about 0.2 moles, most preferably about 0.001 to about 0.1 moles, of the gold-complexing agent per liter of eluant. In addition, preferably the eluant has a pH in the range of about 5 to about 7, is non-toxic and is isotonic.

The method according to the invention may be practiced most successfully by using suitably selected combinations of adsorption agents for the $^{195m}$Hg parent isotope and eluants for the $^{195m}$Au daughter radioisotope. Presently preferred combinations of adsorption agents and eluants are set forth in Table I, the listed adsorption agents being the named mercury ion-binding material on a substrate material of silica gel, controlled pore glass, other porous substrate material, or solid glass beads.

TABLE I

| Adsorption Agent-Substrate Material | Eluant-Aqueous Solution of |
|---|---|
| zinc sulphide | thiosulphate |
| hydrate manganese dioxide | tris(hydroxymethyl)-aminomethane |
| hydrated manganese dioxide | hippurate |
| silver sulphide | glutathione |
| silver sulphide | thiomalate |
| silver | glutathione |
| silver | mercaptopropionyl glycine |
| silver | thiomalate |
| anchored ligand having thiol terminal functional groups | thiosulphate |
| anchored ligand having amino terminal functional groups | tris(hydroxymethyl)-aminomethane |

Of the above combinations set forth in Table I, the combination of a zinc sulphide containing adsorption agent and a thiosulphate containing eluant is presently most preferred.

By eluting an adsorption agent charged with $^{195m}$Hg in accordance with the present invention, a $^{195m}$Au-containing liquid is obtained which is very suitable to perform a radiodiagnostic examination, for example, an examination into deviations in the form and function of the internal organs such as the heart of an animal, particularly a warm-blooded animal such as a human.

As was mentioned previously, since a $^{195m}$Au radioisotope has a half-life of only about 30 seconds, the radioisotope must be produced at approximately the same location where it is to be used. A known device for producing radioactive compounds is a radioisotope generator which can be accommodated, for example, in a hospital or in a clinical laboratory, and from which a liquid containing a daughter radioisotope can be obtained when necessary by elution from the parent isotope contained within the generator. The present invention therefore also relates to a particular type of radioisotope generator in which a $^{195m}$Au-containing liquid can be prepared, the generator-comprising a column filled with the above-described adsorption agent upon which $^{195m}$Hg can be adsorbed and $^{195m}$Au subsequently eluted. The column furthermore comprises an inlet aperture for the eluant and a tapping point for the eluate. When the eluate is introduced directly into the body of a patient, essentially the entire generator system must of course be sterile.

In conducting experiments with a number of radioisotope generators packed with some of the aforementioned adsorption agents and loaded with $^{195m}$Hg, it has been found that with some of the previously described adsorption agent/eluant combinations, lower elution yields were observed than were found in the model experiments using the same combinations such as those described in Example II hereinafter. It has been also found that, where observed, such differences between the elution yield simulated in the model experiments and elution yield obtained from generators utilizing the actual parent-daughter isotope pair may be caused by a variety of reasons.

To illustrate some of the typical situations and the reasons causing the observed effects in elution yield, two of the formerly described adsorption agent/eluant combinations, namely a silica based substrate material modified with anchored thiol terminal functional groups in combination with thiosulphate as an eluant and silica based substrate material modified with a metal sulphide such as zinc sulphide in combination with thiosulphate as an eluant may be used as representative examples for further amplification. The first combination illustrates a generator system in which an actual lower elution yield may be related to the quality and properties of the adsorption agent. When utilizing an adsorption agent which has very strong adsorption for mercury ions, or in other words, very strong affinity for mercury ions, but which shows a moderate affinity to gold ions, a situation may appear where a gold ion-complexing eluant has to compete with the adsorption agent for the formed gold ions in the generator to make the ions available for elution. Such competitive processes or competitive reactions will naturally depend on the respective affinities of the adsorption agent and the eluant for the formed gold ions in the generator. The result of such processes, irrespectively of their complexity, is, to the end, given by the overall balance of the respective competitive reactions, that is, by the fraction of elutable gold ions, i.e., elution yield. When the overall balance acts more in favor of the adsorption agent, lower elution yields will result. Conversely, when the overall balance acts more in the favor of the eluant, higher elution yields will result.

It has now been found that even in the negative siutation, that is, when the balance of competitive processes favor the adsorption agent more, the balance may be, by appropriate treatment of the generator system, reversed in such a way that the relatively low elution yields can be remarkably improved. Such treatments to improve the elution yield may be, for example, a deactivation of the adsorption agent, that is, a treatment in which the affinity of the adsorption agent for gold ions is suppressed to the desired degree while the affinity for mercury ions is still maintained at a high level. Such treatments may comprise converting a fraction of, for example, the thiol terminal functional groups to less reactive groups by means of one or more suitable chemical reactions such as substitution, cleavage, condensation and the like. A particularly useful treatment may be oxidation for which a number of known reactions can be employed, for example, oxidation with iodine, bromine, chromic acid, permanganate or with any other known oxidation agent.

When it is desirable to remove the byproduct of the oxidation such as, for instance, manganese dioxide resulting from the treatment with permanganate, another suitable reaction such as a reduction reaction can be employed to dissolve the byproduct and to remove it from the generator by means of washing the column with a suitable liquid. Thus, for removal of manganese dioxide, particularly suitable reduction agents include salts of hydroxylamine, salts of hydrazine, sulphites or sulphurous acid, ascorbates or ascorbic acid, oxalic acid or oxalates, in particular potassium hydrogen oxalate, or any other known reduction agent. After removal of the excess reduction agent and reaction products from the generator by washing the column with a suitable liquid, the generator can be eluted according to the aforesaid manner to obtain a $^{195m}$Au containing eluate having a radioactivity considerably higher than that obtained from the same generator not subjected to the above-described treatment.

In the previously mentioned second combination, that is, an adsorption agent of a silica substrate material modified with a metal sulphide, in particular, with zinc sulphide, another effect was observed, that is, a situation where the elution yield of daughter radioisotope $^{195m}$Au may be related to the amount of radioactivity present in the generator column. This effect, which is manifested by lower elution yield or decrease in elution yield when the generator column is loaded with higher activity of the parent isotope $^{195m}$Hg, is not uncommon. The same effect has also been observed in other radioisotope generators, a typical example being, for example, the well-known technetium generator. It is well established that such a phenomenon is caused by socalled radiation effects which can contribute to a conversion of certain fraction of the daughter radioisotope to a chemical form which has a strong affinity for the adsorption agent used and which is therefore no longer elutable.

By means of a suitable formulation of the eluant, however, it is possible to counteract the chemical changes caused by radiation effects and to improve the elution yield even in generators loaded with high activity of the parent isotope. A well-known example of such counteractive measures in the case of a technetium generator is the addition of oxygen or other oxidation agent to the eluant as described, for example, in U.S. Pat. No. 3,664,964, to improve the elution yield. Similar measures can be applied to the radioisotope generator systems of the present invention.

It has also been found that the decrease in radioactivity in the eluant can be suppressed by the addition of a suitable radical scavenger to the eluant. Suitable radical scavengers include organic hydroxy compounds, for example, glycose or polyethylene glycol, nitrates or nitrites, preferably, however, an alkali or alkaline earth metal nitrate or nitrite such as, for example, sodium nitrate. The quantity of radical scavenger included in the eluant may vary within wide limits, for example, from about 0.0001 to 5% wt./vol being presently preferred. For example, the addition of about 1% sodium nitrate to the eluant improved the elution yield of the generator in such manner that a charge with $^{195m}$Hg up to a radioactivity of more than about 20 mCi is possible without a noticeable decrease of the eluted activity being found. For practical applications, charging of the generator with $^{195m}$Hg with a radioactivity of about 1–300 mCi, preferably from about 20–160 mCi, is generally suitable. The resulting eluate containing the $^{195m}$Au radioisotope is free or substantially free from gold carrier, is non-toxic, and is of a pharmaceutically acceptable quality.

Due to the relatively short half-life of $^{195m}$Au, it generally is advantageous to administer the eluate into a patient to be examined as soon as possible after elution of the generator. The generator is therefore preferably constructed such that a sterile eluate is produced and a direct connection to the patient is possible. A particularly preferred radioisotope generator is one which can be included in a closed system and which contains one or more of the following devices: (a) a reservoir containing the eluant, (b) a pumping device which may be used to both elute the generator and force the resulting eluate into a patient's body, (c) a formulating reservoir with associated mechanism from which a formulating liquid can be added to the eluate, and (d) a flexible tube which is connected at one end to the above mentioned devices and at its other end includes a member adapted to be connected to an auxiliary means normally used in a hospital or clinic to allow a liquid to flow into the blood vessels or body cavities of a patient.

An example of such a radioisotope generator is illustrated in FIG. 1 of the drawing. As shown, radioisotope generator 10 includes generator column 12 essentially completely surrounded by shielding elements 14, e.g. lead, to prevent emissions of radioactivity. Generator column 12 comprises generally cylindrical housing 16 of glass or the like having each end closed by sealing assembly 18 which includes pierceable elastomeric stopper 20 and overlying metal cap 22 having centrally located aperture 24 therein. A bed of particulate adsorption agent 26 contained within housing 16 is confined by filter 28 bonded to the housing.

Upper sealing assembly 18 is pierced by needle 30 which is attached to coupling 32 located on the exterior of shielding element 14 and maintained in position by elastomeric plug 33. Releasably attached to coupling 32 is eluant reservoir 38 having piston 40 and associated plunger 42 for manually forcing eluant from the reservoir, through needle 30, and into column 12. Cap 44 is provided on the upper portion of reservoir 38 to allow the eluant supply in the reservoir to be replenished.

Lower sealing assembly 18 of column 12 is pierced by eluate conduit 34 which projects externally of shielding element 14 and terminates at fitting 36. Releasably attached to fitting 36 of eluate conduit 34 by appropriate complementary fitting 46 is tube 48 of flexible material such as an organic polymeric material. Tube 48 terminates with fitting 50 which is adapted to mate with an administration needle (not shown) of the type customarily used to inject a substance into the body of a patient. Formulating reservoir 52 is attached to eluate conduit 34 by means of formulating conduit 53 containing stopclock 54. Formulating reservoir 52 is adapted to contain a formulating liquid which may be added to the eluate from column 12 so as to alter the eluate composition to produce, for example, a pharmaceutical composition having different or additional effects when administered to a patient or a pharmaceutical composition having greater compatibility with bodily fluids in terms of physiologically acceptable pH, isotonicity, etc.

$^{195m}$Au is useful in a variety of diagnostic tests and is especially suitable for cardiological examinations due to its short half life. It can be used, for example, to evaluate movement of the ventricular walls of the heart and to perform quantitative measurements of various heart functions such as ejection fraction computations.

Serial assessment of left ventricular ejection fraction during various stages of exercise by a patient using the multi-gated cardiac blood pool technique has been reported by Caldwell et al., *Circulation* 61:610 (1980). For exercise studies, however, sequential first pass radionuclide angiocardiography using $^{195m}$Au is more advantageous. In the latter tests, data are acquired over a short time period utilizing only 3–5 cardiac cycles; thus, it is reasonable that they approximate true left ventricular function during peak exercise more closely than data acquired over several hundred heart beats. In addition, body motion during exercise has a major degrading effect on the quality of equilibrium blood pool studies.

The short half-life of $^{195m}$Au and the minimal amount of $^{195m}$Au in the eluate result in low background activity and allows rapid sequential determinations of left ventricular ejection fraction. Determination may be made at time intervals of less than one minute apart.

A further advantage is that even when left ventricular performance is determined during each stage of exercise, the total radiation dose to the patient is significantly reduced compared to that with a single dose of the conventional radiotracer, $^{99m}$Tc. Compared to an equivalent dose of $^{99m}$Tc, $^{195m}$Au exposes the kidneys to five times less, and the whole body to twenty times less, radiation.

The short half life of $^{195m}$Au not only enables monitoring of left ventricular function of short time intervals but also allows simultaneous analysis of myocardial perfusion using $^{201}$Tl. Once the conventional tracer $^{99m}$Tc is administered to a patient, technically acceptable images generally can not be obtained with $^{201}$Tl imaging for at least 24 hours. When $^{195m}$Au is given to a patient, however, $^{201}$Tl injected at peak exercise can be imaged without difficulty after discontinuation of exercise, even after multiple injections of $^{195m}$Au (see Example 24). Therefore, both the functional response to exercise and the presence of exercise-induced myocardial ischemia, as well as $^{201}$Tl myocardial kinetics, may be addressed during a single exercise session. This combined technique also has obvious advantages as far as cost effectiveness of patient evaluation is concerned, since only one exercise test is needed to obtained this information. Even with the development of $^{99m}$Tc-labeled myocardial perfusion imaging agents this combined approach would be feasible because of the difference in primary photopeak of the radionuclides.

Various aspects of the invention will now be described in greater detail with reference to the following examples. It should be understood that the examples are given for the purpose of illustration only.

EXAMPLE I

The adsorption capability of a number of adsorption agents for radioactive mercury ions was determined at various pH levels. The results are summarized in Table A.

For each determination, a solution of $^{195m}$Hg in nitric acid was prepared and the solution then brought to the desired pH in the range of 3–10 by the addition of a base. The resultant solution contained about 4 ug of Hg/ml and had a radioactivity of about 10,000 pulses/sec/ml measured with a gamma counter. About 5 ml of solution and about 0.5 g of a particular adsorption agent were then shaken overnight in a glass vial and then centrifuged. After separation of the particulate material from the supernatant liquid, the radioactivity compared with a standard solution containing no adsorption agent. Each determination was conducted in triplicate.

The various adsorption agents examined were prepared as follows and in each instance, the silica gel used had a 60A porosity and a particle size in the range of about 0.063 to about 0.200 mm. Prior to preparing each adsorption agent, the silica gel was purified by slurrying with conentrated hydrochloric acid, and after standing overnight, washing with additional hydrochloric acid, washing with distilled water, filtering and then drying at about 105° C. in a vacuum oven.

SiO$_2$—ZnS

Dry silica gel was treated with an aqueous solution containing 5% zinc chloride. Other water-soluble zinc salts such as zinc nitrate, zinc sulphate and zinc acetate could have been used equally as well. The excess liquid was filtered off from the resulting slurry after which the moist silica gel cake was reacted with an excess of an aqueous solution of a sulphide. Any water-soluble sulphide is suitable for this purpose, as well as, and even in particular, hydrogen sulphide, both gaseous and in an aqueous solution. Alternatively, soluble thiosulfates or some organic sulphur-containing compounds which decompose in aqueous solutions to yield sulphur, thiol radicals or hydrogen sulphide such as thioacetamide, alkaline thiourea and the like are equally as useful to produce zinc sulphide. After decanting, washing with water and drying in a vacuum, a modified silica gel was obtained which, dependent on the treatment, contained about 0.1–20 mg of ZnS, preferably about 0.8–10 mg., of ZnS per gram of silica gel.

SiO$_2$—AgS

In a corresponding manner, silica gel modified with silver sulphide was prepared. Silica gel was modified with silver by a treatment with silver nitrate solution followed by reduction with ascorbic acid.

SiO$_2$—HMDO

Silica gel modified with hydrated manganese dioxide (HMDO) was prepared by adding a solution of 1.0 M manganese sulphate to the silica gel particles, heating the resulting slurry at about 90° C. and then dropwise adding a heated aqueous potassium permaganate solution. Thereafter, the slurry was decanted and the solids repeatedly washed with dilute nitric acid. The slurry was then filtered, washed with water, and dried at about 60° C. in a vacuum oven.

Another mode of preparing silica gel modified with HDMO consists of the successive addition of an aqueous permaganate solution and a 30% hydrogen peroxide solution to the silica gel particles and then following the remainder of the above procedure.

SiO$_2$—SH

Chemically bound SH-containing functional groups were provided in silica gel by treating dry silica gel with 10% solution mercaptopropyl trimethoxysilane in a polar organic solvent such as acetonitrile in the presence of small amount of diluted mineral acid such as hydrochloric acid to form a slurry. After reacting for about ten minutes and then filtering, washing, and drying in a vacuum, a silica gel was obtained which had mercaptopropyl groups chemically bound at the surface.

SiO$_2$—NH$_2$

In a corresponding manner to the SiO$_2$—SH adsorption agent, chemically-bound, NH$_2$-functional containing groups were provided in silica gel by the reaction of silica gel with a mixture of a 10% solution of N-(2-aminoethyl-3-aminopropyl)trimethoxysilane in water and a 0.1% aqueous acetic acid.

In Table A below, the experimentally determined average distribution coefficient K$_D$ for the radioactive material are set forth for each adsorbtion agent. K$_D$ is defined as:

$$K_D = \frac{\text{pulses prior to adsorption}}{\text{pulses after adsorption}} - 1 \times \frac{ml}{g}$$

A high K$_D$-value thus indicates that $^{195m}$Hg has been efficiently adsorbed on the adsorption agent. For example, a K$_D$-value of $10^3$ indicates that at least about 99% of the mercury has been adsorbed and a K$_D$-value of $10^4$ indicates that at least about 99.9% of the mercury has been adsorbed by the adsorption agent. In addition, peak adsorption for a particular adsorption agent generally occurs at nearly a neutral pH or at relatively low acidity. From the table it is apparent that, at a suitable pH, the adsorption agents examined are capable of adsorbing essentially all of the $^{195m}$Hg.

TABLE A

| pH | SiO$_2$ HMDO | SiO$_2$ ZnS | SiO$_2$ AgS | SiO$_2$ Ag | C | SiO$_2$—SH | SiO$_2$—NH$_2$ |
|---|---|---|---|---|---|---|---|
| 3 | 16 | $4.6 \times 10^3$ | $1.1 \times 10^4$ | $6.4 \times 10^3$ | $5.5 \times 10^4$ | $2.2 \times 10^3$ | $2.8 \times 10^3$ |
| 4 | $4.2 \times 10^3$ | $5.3 \times 10^3$ | $2.3 \times 10^4$ | $5.8 \times 10^3$ | $5.8 \times 10^5$ | $2.5 \times 10^3$ | $2.7 \times 10^3$ |

TABLE A-continued

| | Adsorption agent | | | | | | |
|---|---|---|---|---|---|---|---|
| pH | $SiO_2$ HMDO | $SiO_2$ ZnS | $SiO_2$ AgS | $SiO_2$ Ag | C | $SiO_2$—SH | $SiO_2$—$NH_2$ |
| 5 | $4.2 \times 10^3$ | $2.2 \times 10^3$ | $1.3 \times 10^4$ | $3.8 \times 10^3$ | $1.1 \times 10^5$ | $2.2 \times 10^3$ | $3.1 \times 10^3$ |
| 6 | $4.4 \times 10^3$ | $4.3 \times 10^3$ | $4.0 \times 10^3$ | $2.0 \times 10^3$ | $1.6 \times 10^4$ | $2.5 \times 10^3$ | $3.3 \times 10^3$ |
| 7 | $4.7 \times 10^3$ | $3.2 \times 10^3$ | $5.1 \times 10^3$ | $9.5 \times 10^2$ | $1.3 \times 10^5$ | $3.1 \times 10^3$ | $3.4 \times 10^3$ |
| 8 | $4.3 \times 10^3$ | 33 | $1.5 \times 10^3$ | $5.0 \times 10^2$ | $1.0 \times 10^5$ | $1.8 \times 10^3$ | $3.5 \times 10^3$ |

EXAMPLE II

The suitability of the previously mentioned preferred combinations of adsorption agents and eluants are illustrated by the experiments set forth in the following. In conducting these experiments, the isotope $^{203}$Hg was used instead of the parent isotope $^{195m}$Hg and the isotope $^{98}$Au instead of the daughter radioisotope $^{195m}$Au. This substitution was made to the practical considerations that (1) experiments with $^{195m}$Au are impractical because of its short half-life, and (2) $^{195m}$Au would be formed continuously from $^{195m}$Hg which would impede the interpretation of the results. The experiments performed, however, provide an equally good representation of the distribution of mercury and gold ions over the adsorption agent and the eluate since, as is generally recognized, the various isotopes of the same elements do not differ in physical and chemical properies such as solubility, adsorption, and the like.

The experiments were conducted as follows: About 500 mg of the adsorption agent to be tested was loaded in an adsorption column and was charged with $^{203}$Hg ions as described previously to simulate charging with $^{195m}$Au-containing liquid. The eluant liquids used were prepared by dissolving a quantity of 1-3 ug of gold containing $^{198}$Au in 1 ml of an aqueous solution having a pH of about 5-6 and containing 0.001-0.1 molar of one of the gold ion complexing agents set forth in Table B. The elution was conducted by adding about 50 ml of the eluant liquid on the upperside of the filled column and collecting the eluate on the lower side in fractions of about 5 ml. The quantity of gold used per column in each experiment was much smaller than the overall capacity of the adsorption agent for noncomplexed gold. The radioactivity in the eluate was determined by means of a gamma counter. In Table B, the percentage of $^{198}$Au which was not adsorbed on the adsorption agent is recorded. The radionuclidic purity of the eluate was determined by gamma-spectrometry. In all experiments recorded in Table B, less than 0.1% of $^{203}$Hg was present in the eluate. The experiments were conducted either in duplicate or triplicate.

The following average results were obtained.

TABLE B

| | gold ion-complexing agent | | | | | |
|---|---|---|---|---|---|---|
| adsorption agent | thiosulfate | tris(hydroxymethyl)-aminomethane | hippurate | glutathione | mercaptopropionyl glycine | thiomalate |
| $SiO_2$ HMDO | | ca 90% | 50% | | | |
| $SiO_2$ ZnS | 91% | | | | | |
| $SiO_2$ $Ag_2S$ | | | | over 80% | | over 60% |
| $SiO_2$ Ag | | | | ca 95% | 88% | over 95% |
| $SiO_2$—SH | ca 70% | | | | | |
| $SiO_2$—$NH_2$ | | over 80% | | | | |

EXAMPLE III

An adsorption agent comprising silica gel and zinc sulphide is prepared.

The silica gel is prepared by suspending about 50 g of silica gel having a particle size in the range of about 0.063–0.200 mm and a mean pore diameter of about 60Å in concentrated hydrochloric acid and allowing the suspension to stand overnight. The following day, the slurry is filtered through a sintered glass filter and the wet cake then is washed with distilled water until the filtrate is neutral. The purified silica gel is then dried at about 105° C. in a vacuum oven. The dried, acid prewashed silica gel is then treated with an excess of 5% aqueous solution of zinc chloride to form a slurry. After filtering the slurry, a moist cake of silica gel saturated with zinc chloride is obtained. The resulting pretreated silica gel is added in portions to an excess of a saturated solution of hydrogen sulphide in about 500 ml of 0.02 N acetic acid while the solution is being stirred and hydrogen sulphide passed therethrough. After stirring for about another 10 minutes, the slurry is decanted and washed several times with warm water. The silica gel is then treated once again in the same manner with a solution of hydrogen sulphide in dilute acetic acid. After washing with water and then filtering, the silica gel product is dried in a vacuum maintained furnace at about 80° C. The dried adsorption agent is placed in a closed bottle and treated overnight on the Mini-roll mill to remove the loosely adhering zinc sulphide particles. The agent is again suspended in water and washed by repeated decantations with water until the supernate remains completely clear. After filtration and rinsing with water, the agent is again dried at about 80° C. in a vacuum oven. The obtained adsorption agent contains about 6.3 mg ZnS per gram of agent as determined by complexometric titration.

EXAMPLE IV

An adsorption agent comprising controlled pore glass and zinc sulphide is prepared.

About 20 g of dry, acid prewashed, controlled pore glass substrate material known as CPG-10-500 having a mesh size 120/200 and mean pore diameter of about 530Å is slurried in an excess of about 2% aqueous solution of zinc chloride and the slurry is outgassed under vacuum. Thereafter, the slurry is treated in the manner as described in Example III. The adsorption agent obtained contains about 5.5 mg ZnS per gram of the agent as determined by photometric determination.

EXAMPLE V

An adsorption agent comprising controlled pore glass and zinc sulphide is prepared.

About 10 g of dry, acid prewashed controlled pore glass substrate material as in Example IV is slurried in an excess of a 5% aqueous solution of zinc chloride and the slurry outgassed under vacuum. The slurry obtained is poured into a larger glass chromatographic column having sintered glass filter at the bottom. The excess liquid is drained off by means of a mild vacuum so that the column remains filled with wet, pretreated glass particles. Hydrogen sulphide gas is introduced into the column under mild pressure and is allowed to pass through the column for about 15 minutes. After the reaction is complete, the excess free hydrogen sulphide is removed by a stream of air and the wet material transferred from the column into a beaker and slurried in water. The slurry is repeatedly washed by decantations with water, filtered and dried at about 80° C. in vacuum oven. The adsorption agent obtained is further treated in the manner described in Example III. The adsorption agent obtained contains about 1.65 mg ZnS per gram of agent as found by photometric determination.

EXAMPLE VI

An adsorption agent comprising a substrate material and zinc sulphide is prepared.

About 10 g of pellicular HPLC adsorbent sold under the trademark Chromosorb LC-2 (Johns-Manville product) is slurried in an excess of a 5% aqueous solution of zinc acetate and the slurry is outgassed under vacuum. The obtained slurry is treated further in the manner as described in Example V. The adsorption agent obtained contains about 5.5 mg ZnS per gram of the agent as found by photometric determination.

EXAMPLE VII

An adsorption agent comprising solid glass beads and cadmium sulphide is prepared.

About 5 g of dry, acid prewashed, solid glass pearls of about 0.15–0.18 mm size are suspended and then spread over a large area in a vessel containing aqueous solution $1 \times 10^{-3}$M cadmium chloride, 1 M ammonia, $1 \times 10^{-2}$M NaOH and $6 \times 10^{-3}$M thiourea. The glass pearls are left standing in the solution for about 48 hours with occasional movement of the pearls such that they remained spread over large area and in a single layer. Thereafter, the glass pearls are filtered, washed with water and ethanol and then dried at about 80° C. in the vacuum oven.

The adsorption agent obtained is then examined under a microscope. All the glass pearls appeared to be homogenously covered with a smooth and compact film of cadmium sulphide, the thickness of which is estimated to be less than about 1 μm.

EXAMPLE VIII

An adsorption agent comprising solid glass beads and a thin layer containing zinc sulphide thereover is prepared.

About 5 g of dry, acid prewashed, solid glass pearls of a size of about 0.15–0.18 mm together with a mixture of dry, very fine zinc sulphide powder and zinc oxide powder in weight ratio of about 1:1 are placed in a closed bottle containing several small Teflon bars and tumbled on a Mini-roll mill overnight. The product obtained is then suspended in water, washed by repeated decantations with water till the supernate remains completely clear, and then dried in a vacuum oven at about 80° C.

The adsorption agent obtained is examined under a microscope. All pearls examined appear to be covered with a layer of zinc sulphide-zinc oxide particles pressed onto the surface of the pearls. The homogenity of the layers is, however, less perfect than that obtained according to preceeding Example VII.

EXAMPLE IX

An adsorption agent comprising silica gel and anchored thiol terminal functional groups is prepared.

To about 100 ml of 10% (v/v) solution of mercaptopropyltrimethoxysilane in acetonitrile, about 5 ml of 1N HCl is added. The reaction mixture obtained is, after homogenization, immediately poured onto about 50 g of dry, acid prewashed silica gel prepared as in Example III thereby forming a slurry in the reaction mixture. The reaction is allowed to proceed for about 10 minutes at room temperature under slow stirring. The slurry is then filtered through a glass filter, washed with three portions (50–75 ml) of acetonitrile and the resulting solid product dried overnight at room temperature under a vacuum. The adsorption agent obtained is analyzed for the content of free SH groups using iodometric titration. Results show about $14 \pm 1$ mg SH per gram of the adsorption agent.

EXAMPLE X

A $^{195m}$Au-containing liquid is generated in a radioisotope generator.

A radioisotope generator made by providing a small glass tube which is closed on its lower end by a sintered glass filter and filling the tube with about 500 mg of modified silica gel which functions as an adsorption agent for the parent isotope. The silica gel is produced by the method set forth in Example III. The adsorption agent is confined in the column by closing the open end of the tube with a porous plastic filter maintained in place by a retaining ring of silicone rubber. The column is then sealed at both ends by discs of silicon rubber and aluminum caps.

After filling the column with the modified silica gel, the column is charged with $^{195m}$Hg by contacting the modified silica gel adsorption agent with a solution of radioactive mercury nitrate having a pH of about 5–6, the solution having been obtained by dissolving about 14 mCi $^{195m}$Hg is obtained from a cyclotron target in about 2 ml of concentrated nitric acid, then diluting the resulting concentrate with water to approximately 10 ml, and finally adjusting the pH to about 5–6.

In charging the column with the radioactive $^{195m}$Hg isotope, the column is inverted so that the sintered glass filter is on the top of the column and thereafter the adsorption agent contained in the column is contacted with the isotope containing charging solution by allowing the solution to flow into the column through the sintered glass filter. By charging the column in this manner, incidental adsorption of $^{195m}$Hg on the plastic construction parts of the column is thereby avoided. The adsorption of $^{195m}$Hg on the adsorption agent is practically quantitative, with no more than about 0.009% of the applied activity being found in the column effluents after the charging has been completed.

An eluant for the column is prepared by dissolving about 29.8 g of sodium thiosulphate (5H$_2$O) and about 10 g of sodium nitrate in about 1000 ml of water. The radioisotope generator column is eluted in the inverted position by injecting about 2 ml of the eluant into the generator column under pressure. In a very short time, approximately 2 to 3 seconds, the $^{195m}$Au-containing eluate could be drained from the column. The eluate has a radioactivity of about 8 mCi. After 3 to 5 minutes later, the column can be eluted again. In each elution, approximately 60% of the theoretically available $^{195m}$Au can be eluted from the generator.

The number of millicuries in the eluate is derived from the count rate of the eluate measured on a fast, single channel gamma analyzer using the gamma energy channel of 261 keV. The obtained count rate is (next to usual geometry, efficiency and dead time correction factors) corrected for the loss of counts due to decay of $^{195m}$Au during the counting time and is also corrected for the loss of activity in the time elapsed between elution and the start of counting for each eluate. The resulting corrected count rate of each eluate is compared with a count rate of an aliquot standard sample of charging solution containing $^{195m}$Hg and $^{195m}$Au isotopes in the decay equilibrium, again counting gamma rays at 261 keV. From this comparison of count rates are derived the elution yield and the number of millicuries of $^{195m}$Au in the obtained eluate by taking into account the ratio of emission rates of 261 keV gamma rays between $^{195m}$Au isotope in a pure form and between $^{195m}$Hg in decay equilibrium with $^{195m}$Au being 0.88–0.90.

Similarly, $^{195m}$Hg breakthrough in the eluate, that is, radionuclidic purity of the eluate, is determined (after complete disappearance of eluted $^{195m}$Au) by counting the 261 keV gamma rays emitted by the $^{195m}$Au formed in equilibrium from the remaining $^{195m}$Hg, the net count rate being again compared with the standard sample of the $^{195m}$Hg/$^{195m}$Au charging solution. In all measurements, the radionuclidic purity proves to be better than 99% which indicates substantially no contamination of the eluate with the parent isotope. The maximum contamination found in eluates obtained from a number of generators prepared according to this Example is approximately 0.3–0.4% of $^{195m}$Hg during the first elution of the generator immediately after charging or, when the generator had been charged the day before, during the first elution the next morning. The contamination with $^{195m}$Hg drops during subsequent elutions to about 0.05 to 0.1%.

The generator described herein is eluted at various intervals over a period of days, the shortest interval between elutions being about 5 minutes. The values given below illustrate the functions of the generator, the values being elution yield (Y), number of millicuries obtained per elution (the values decreasing accordingly with the decay of parent isotope), and the radionuclidic purity (RN) in % of $^{195m}$Hg breakthrough found in the obtained eluates:

| Elution day | Elution number | Y (%) | mCi | RN (%) |
|---|---|---|---|---|
| 1 | 1 | 60 | 8.3 | 0.13 |
|  | 2 | 63 | 8.8 | 0.04 |
|  | 3 | * | * | 0.05 |
|  | 4 | * | * | 0.06 |
| 2 | 1 | 57 | 5.4 | 0.25 |
|  | 2 | 59 | 5.7 | 0.09 |
| 3 | 1 | 50 | 3.3 | 0.38 |
|  | 2 | 56 | 3.6 | 0.14 |
|  | 3 | 56 | 3.6 | 0.07 |

*not measured, eluates were used for phantom experiments

Another generator prepared as described in this Example which is charged with about 11.7 mCi of $^{195m}$Hg gives the following values upon repeated elution;

| Elution day | Elution number | Y (%) | mCi | RN (%) |
|---|---|---|---|---|
| 1 | 1 | 60 | 7.0 | 0.22 |
|  | 2 | 66 | 7.1 | 0.13 |
|  | 3 | 70 | 7.6 | 0.06 |
|  | 4 | 70 | 7.6 | 0.05 |
| 2 | 1 | 60 | 5.0 | 0.34 |
|  | 2 | 66 | 5.5 | 0.11 |
|  | 3 | 65 | 5.5 | 0.09 |
|  | 4 | 62 | 4.8 | 0.11 |
|  | 5 | 66 | 5.2 | 0.07 |
| 3 | 1 | 59 | 3.5 | 0.10 |
|  | 2 | 57 | 3.4 | 0.04 |
|  | 3 | 57 | 3.4 | 0.04 |
|  | 4 | 57 | 3.2 | 0.04 |
|  | 5 | 58 | 3.2 | 0.03 |
| 6 | 2 | 59 | 1.0 | 0.05 |
|  | 3 | 59 | 1.0 | 0.04 |

Yet another generator prepared as described in this Example but containing other batch of adsorption agent according to Example III which includes about 6.2 mg ZnS per gram of the agent and which is charged with about 83 mCi of $^{195m}$Hg gives the following values upon repeated elution:

| Elution day | Elution number | Y (%) | mCi | RN (%) |
|---|---|---|---|---|
| 1 | 1 | 50 | 41.7 | 0.35 |
|  | 2 | 50 | 41.8 | 0.21 |
|  | 3 | 50 | 41.8 | 0.15 |
|  | 4 | 51 | 42.7 | 0.13 |
|  | 5 | 48 | 41.0 | 0.11 |
|  | 6 | 47 | 39.3 | 0.09 |
| 2 | 1 | 54 | 33.3 | 0.20 |
|  | 2 | 53 | 32.7 | 0.14 |
|  | 3 | 51 | 31.5 | 0.10 |
|  | 4 | 48 | 29.5 | 0.07 |
|  | 5 | 50 | 29.1 | 0.09 |
|  | 6 | 51 | 29.7 | 0.07 |
|  | 7 | 51 | 29.7 | 0.05 |
|  | 8 | 50 | 29.6 | 0.05 |
|  | 9 | 50 | 29.6 | 0.05 |
|  | 10 | 53 | 30.3 | 0.11 |
|  | 11 | 52 | 29.6 | 0.06 |
|  | 12 | 51 | 29.3 | 0.05 |
| 3 | 7 | 51 | 20.0 | 0.18 |
|  | 8 | 50 | 19.3 | 0.07 |
|  | 9 | 51 | 20.0 | 0.06 |

EXAMPLE XI

A $^{195m}$Au-containing liquid is prepared.

A generator is prepared as described in Example X except that an adsorption agent prepared according to Example IV is used. The generator is charged with about 3.8 mCi of $^{195m}$Hg and eluted in the manner of Example X. The following values are obtained upon repeated elution:

| Elution day | Elution number | Y (%) | RN (%) |
|---|---|---|---|
| 1 | 1 | 49 | 0.16 |
|  | 2 | 48 | 0.07 |
|  | 3 | 49 | 0.03 |

| Elution day | Elution number | Y (%) | RN (%) |
|---|---|---|---|
|  | 4 | 48 | 0.02 |
| 2 | 1 | 55 | 0.06 |
|  | 2 | 54 | 0.03 |
|  | 3 | 54 | 0.02 |
|  | 4 | 54 | 0.02 |

EXAMPLE XII

A $^{195m}$Au-containing liquid is generated.

A generator is prepared according to Example X except that an adsorption agent prepared according to Example V is used. The generator is charged with about 3.8 mCi of $^{195m}$Hg and eluted in the manner of Example X.

The following values are obtained upon repeated elution of the generator:

| Elution day | Elution number | Y (%) | RN (%) |
|---|---|---|---|
| 2 | 1 | 33 | 0.15 |
|  | 2 | 33 | 0.07 |
|  | 3 | 32 | 0.05 |
|  | 4 | 32 | 0.05 |
| 3 | 1 | 36 | 0.11 |
|  | 2 | 35 | 0.07 |
|  | 3 | 35 | 0.07 |

EXAMPLE XIII

A $^{195m}$Au-containing liquid is generated with an eluant containing a gold carrier.

A generator is prepared according to Example X except that an adsorption agent prepared according to Example VI is used. The generator is charged with about 4.8 mCi of $^{195m}$Hg. Elution of the generator on the first day is carried out in the same manner as the elution of the generator as described in Example X but on the second day, the elution is conducted with an eluant of the same composition but further including added gold as carrier in a concentration of about 3 ug Au/ml eluant. On the third day, the generator is eluted with an eluant containing about 10 ugAu/ml as a carrier. The following values are obtained from the elutions:

| Elution day | Elution number | Y (%) | RN (%) |
|---|---|---|---|
| 1 | 1 | 67 | 0.05 |
|  | 2 | 66 | 0.02 |
|  | 3 | 61 | 0.01 |
|  | 4 | 55 | 0.02 |
|  | 5 | 62 | 0.08 |
|  | 6 | 58 | 0.07 |
| 2 | 1 | 59 | 0.11 |
|  | 2 | 59 | 0.12 |
|  | 3 | 56 | 0.13 |
|  | 4 | 56 | 0.13 |
|  | 5 | 53 | 0.14 |
|  | 6 | 55 | 0.13 |
| 3 | 1 | 47 | 0.14 |
|  | 2 | 47 | 0.11 |
|  | 3 | 46 | 0.09 |

EXAMPLE XIV

A generator is prepared according to the procedures of Example X except that an adsorption agent prepared according to Example VII is used. The generator is charged with about 6.0 mCi of $^{195m}$Hg and eluted in the manner described in Example X. The following values are obtained upon repeated elution:

| Elution day | Elution number | Y (%) | RN (%) |
|---|---|---|---|
| 1 | 1 | 30 | 3.9 |
|  | 2 | 27 | 0.18 |
|  | 3 | 26 | 0.09 |
|  | 4 | 25 | 0.07 |
| 2 | 1 | 33 | 0.22 |
|  | 2 | 31 | 0.11 |
|  | 3 | 31 | 0.08 |
|  | 4 | 31 | 0.07 |

EXAMPLE XV

A $^{195m}$Au-containing liquid is generated.

A generator is prepared according to the procedure of Example X except that an adsorption agent prepared according to Example VIII is used. The generator is charged with about 5.8 mCi of $^{195m}$Hg and eluted as described in Example X.

The following values are obtained upon repeated elution:

| Elution day | Elution number | Y (%) | RN (%) |
|---|---|---|---|
| 2 | 1 | 48 | 3.4 |
|  | 2 | 61 | 1.9 |
| 3 | 1 | 58 | 1.1 |
|  | 2 | 57 | 0.5 |
|  | 3 | 58 | 0.8 |
| 6 | 1 | 47 | 2.1 |
|  | 2 | 47 | 0.7 |

EXAMPLE XVI $^{195m}$Au-containing liquids are produced using various deactivated adsorption agents.

Five generators are prepared according to the procedure of Example X except that an adsorption agent prepared according to Example IX is used in each generator. All generators are charged with approximately 5 mCi of $^{195m}$Hg as described in Example X.

Generator 1, which serves as a control, is eluted in the normal manner described in Example X. The following values are obtained:

| Elution day | Elution number | Y (%) | RN (%) |
|---|---|---|---|
| 1 | 1 | 6.3 | 0.10 |
|  | 2 | 5.3 | 0.03 |
|  | 3 | 5.2 | 0.02 |
|  | 4 | 4.3 | 0.02 |
| 2 | 1 | 2.6 | 0.04 |
|  | 2 | 2.3 | 0.02 |
|  | 3 | 2.1 | 0.01 |

After charging, generator 2 is treated by washing the column with the following solutions (in the same sequence given) to effect a chemical deactivation of the adsorption agent:

(a) Potassium permaganate, 0.1 N, 10 ml,
(b) TRISAM pH 5.2, 10 ml (the solution prepared by neutralizing 2.0 ml of concentrated nitric acid, diluted to about 10 ml with water, with an aqueous solution of IM Tris (hydroxymethyl)-aminomethane and 3M ammonia to pH 5.2, and further diluting the resulting solution to about 20.0 ml with water), (c) Saturated solution of potassium hydrogen oxalate, 10 ml,
(d) 0.1M solution of tris (hydroxymethyl)-aminomethane nitrate having pH 8, 10 ml,
(e) normal eluant as described in Example X, 10 ml.

After the above treatment, generator 2 is eluted in the manner described in Example X. The following values are obtained upon repeated elution:

| Elution day | Elution number | Y (%) | Rn (%) |
|---|---|---|---|
| 2 | 1 | 32 | 0.4 |
|  | 2 | 31 | 0.17 |
|  | 3 | 32 | 0.14 |
|  | 4 | 30 | 0.15 |
| 3 | 1 | 31 | 0.35 |
|  | 2 | 31 | 0.14 |
|  | 3 | 29 | 0.11 |
|  | 4 | 29 | 0.09 |
| 7 | 1 | 33 | 0.8 |
|  | 2 | 34 | 0.3 |
|  | 3 | 33 | 0.16 |

After charging, generator 3 is chemically treated by washing with the following solutions:
(a) 5% solution of chromium trioxide in 1% acetic acid, 10 ml,
(b) 0.1M solution of Tris (hydroxymethyl)-aminomethane nitrate having pH 8, 10 ml,
(c) 10% solution of ammonium chloride in ammonia diluted with water 1:1, 10 ml,
(d) TRISAM PH 5.2, 10 ml (composition as given above),
(e) normal eluant as described in Example X, 10 ml.

After the above treatment, generator 3 is eluted in the manner as described in Example X. The following values are obtained:

| Elution day | Elution number | Y (%) | RN (%) |
|---|---|---|---|
| 1 | 1 | 15.7 | 1.20 |
|  | 2 | 20.8 | 0.20 |
|  | 3 | 17.0 | 0.12 |
| 4 | 1 | 17.0 | 0.45 |
|  | 2 | 15.0 | 0.22 |
|  | 3 | 14.0 | 0.10 |

First eluates from this experiment had light yellowish color.

After charging, generator 4 is treated by washing the column with the following solutions:
(a) Potassium permaganate 0.1 N, 10 ml,
(b) TRISAM pH 5.2, 10 ml (composition as given above),
(c) 5% natrium ascrobate pH 4.5, 10 ml,
(d) 0.1M solution of Tris (hydroxymethyl)-aminomethane nitrate having pH 8, 10 ml,
(e) Normal eluant as described in Example X, 10 ml.

After the above treatment, generator 4 is eluted in the manner described in Example X. The following values are obtained from repeated elution:

| Elution day | Elution number | Y (%) | RN (%) |
|---|---|---|---|
| 1 | 1 | 34 | 0.5 |
|  | 2 | 35 | 0.3 |
|  | 3 | 33 | 0.2 |
|  | 4 | 34 | 0.2 |
| 2 | 1 | 19 | 0.3 |
|  | 2 | 19 | 0.04 |
|  | 3 | 19 | 0.07 |
|  | 4 | 19 | 0.07 |

After charging generator 5 is treated by washing with the following solutions:
(a) Potassium permaganate 0.1N, 10 ml,
(b) TRISAM pH 5.2, 10 ml (composition as given above),
(c) 3% hydroxylamine hydrochloride, 10 ml,
(d) 0.1M solution of Tris (hydroxymethyl)-aminomethane nitrate having pH 8, 10 ml,
(e) normal eluant as described in Example X, 10 ml.

After this treatment, generator 5 is eluted in the normal manner as described in Example X. The following values are obtained:

| Elution day | Elution number | Y (%) | RN (%) |
|---|---|---|---|
| 1 | 1 | 30 | 0.5 |
|  | 2 | 31 | 0.2 |
|  | 3 | 30 | 0.1 |
|  | 4 | 30 | 0.1 |
| 2 | 1 | 21 | 0.4 |
|  | 3 | 20 | 0.06 |
|  | 4 | 20 | 0.06 |

From the above experiments with generators 2–5, it is evident that by chemically treating an adsorption agent containing an SH complex-forming ligand, a generator producing high elution yields can be obtained.

EXAMPLE XVII $^{195m}$Au-containing eluate is administered to an experimental animal to determine the efficacy of the eluate in studying left ventricular function such as wall motion and calculation of parameters of function like ejection fraction and to evaluate the visualization of flow through the coronary artery system upon ejection of blood from the left ventricular cavity. The animal chosen for the experiment is a pig due to the similarity between its coronary artery system and that of a human.

A young pig having a weight of about 27.5 kg is anesthetized by intubating, after an intramuscular injection of azaperone, succeeded by an intravenous administration of metidomate, and administering a gaseous mixture of oxygen, nitrous oxide ($N_2O$) and 1–2% halothene. By a small incision, the right jugular vein of the animal is exposed and opened at that area. Through this opening, a Swann-Ganz type catheter is introduced and, under observation by X-ray, is advanced through the right ventricle into the pulmonary artery thereby eliminating right ventricular activity as a source of measured activity. The animal was then positioned under a Searle PhoGamma III gamma camera which is connected to an ADAC computer and provided with a collimator suitable for an average energy level of about 300 KeV. The tapping aperture of the radioisotope generator described in Example X is connected directly to the catheter.

During the subsequent examination, a number of discrete quantities of eluate were administered to the animal. In each administration, about 2 ml of $^{195m}$Au-containing eluate having an activity quantity of about 5–6 mCi is injected through the applied catheter, thereafter followed immediately by about 3 ml of isotonic salt solution so as to rinse all the radioactivity from the catheter and into the circulation system of the animal.

Figure 2:
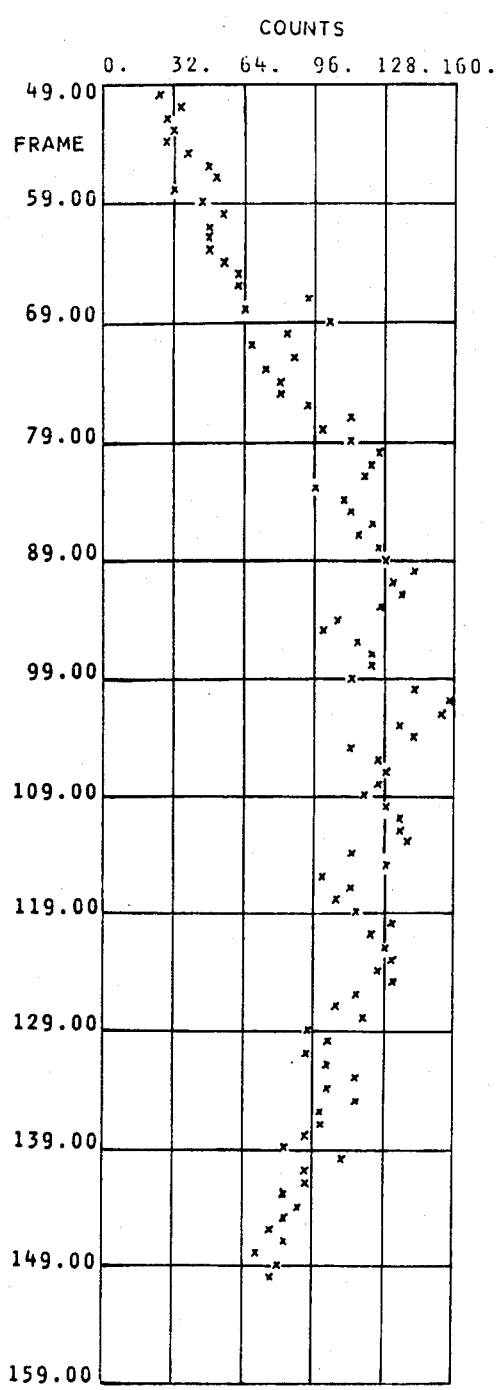
Figure 2:
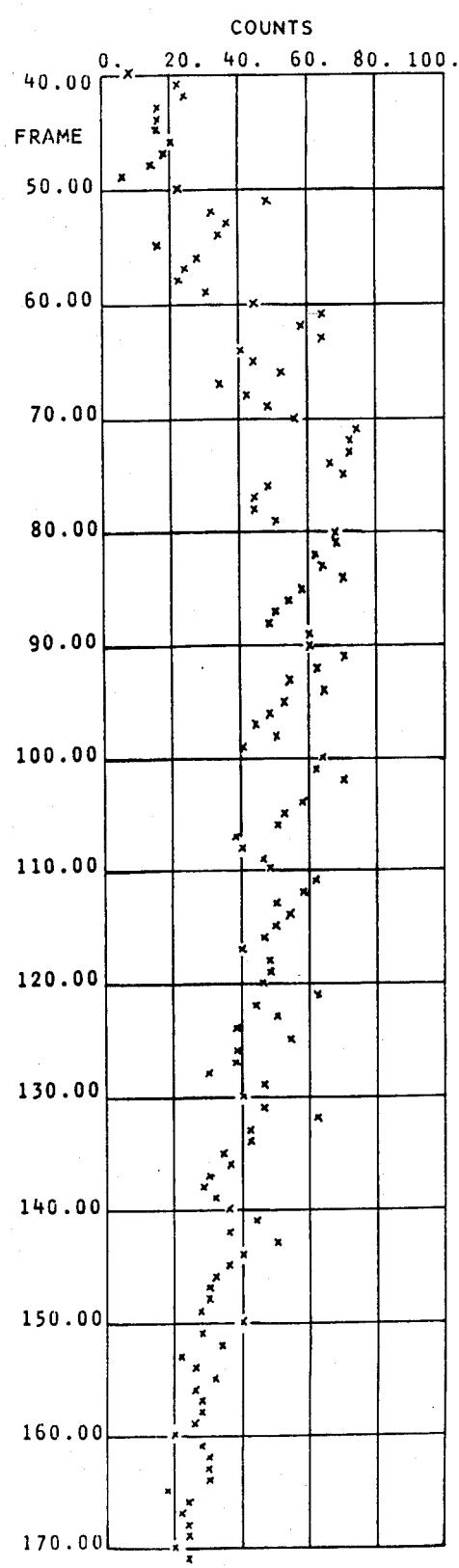

With the animal vetrodorsal position, the administration is conducted 10 times and then two times with the animal in the lateral position. The image information obtained is stored in the computer and studied afterwards. The recorded information is used to prepare curves of the activity variation over various regions of the heart. FIG. 2 of the drawing shows two curves which denote the activity variation above the left ventricle, the left curve with the experimental animal in the ventro-dorsal position, the right curve with the experimental animal in the lateral position. The measured radioactivity in pulses ("counts") is plotted on the horizontal axis. The vertical axis is the time axis where 10 units ("frames") correspond to 0.5 seconds. Regularly recurring undulatory movements of approximately 1 per half second can be observed throughout the length of the curve and these movements represent the contractions of the heart. These curves clearly show the contraction movements of the heart and in addition it is clear that, for example, the 10th study is not disturbed by activity remaining from preceding studies.

From the experimental results, it is observed that the animal under narcosis showed no signs that it could not withstand the twelve direct infusions of $^{195m}$Au-containing eluate and good visual information can be obtained on the location, shape and movement of the left-half of the heart and of the large blood vessels. The information is suitable for determination of the contraction of the ventricular cavity and thus, contraction abnormalities in the heart, if present can be observed. Since the information is obtained from only a few beats of the heart, it is possible to determine changes in heart wall movement during small changes in working conditions such as exercise loads increasing in small increments. The information obtained is of the same type as that which may be obtained from human patients to compute clinically valuable data. The animal experiment therefore illustrates the particular suitability of the $^{195m}$Au generator and $^{195m}$Au-containing eluate for human applications

EXAMPLE XVIII

The procedure set forth in Example XVII was repeated upon another pig having a weight of about 25 kg. However, prior to administration of the $^{195m}$Au-containing eluate, the pig was given about 5–6 mCi pertechnetate after initial injection of pyrophosphate. Upon switching the gamma camera to the 140 keV energy channel, the distribution pattern of the $^{99m}$Tc labelled erythrocytes was used for positioning the heart cavities under the gamma camera. The radiation from $^{99m}$Tc did not influence subsequent measurements from the $^{195m}$Au-containing eluate.

After administration of the $^{195m}$Au-containing eluate through the catheter, the distribution of $^{195m}$Au was measured by performing dynamic studies of about 10.1 sec. during collecting frames of 50 millisec. in a 32×32 memory matrix. These studies were therafter analyzed by adding together all frames in a 10 sec. dynamic study and, with or without consulting the $^{99m}$Tc bloodpool image, mapping out an approximate region of interest of the left ventricle. A time/activity curve of this region was obtained from the computer and, using the standard computer software, the beats of the left ventricle during which the activity bolus passed through the left ventricle were singled out which normally involved four or five beats. Beats of equal length were then added together into one series encompassing one cardiac cycle and subsequently displayed in a movie loop fashion to study wall motions. Ejection fractions were calculated from the frames containing the end-diastolic and end-systolic movements of the cardiac cycle as determined from a time/activity curve of the movie loop.

EXAMPLE XIX

The procedure set forth in Example XVIII was repeated upon another young pig except that the $^{195m}$Au-containing liquid was injected into the right side of the heart instead of bypassing the right side of the heart with a Swann-Ganz catheter by pulling the catheter back into the superior caval vein. The radioactivity administered in each elution of the generator was aobut 25 to 30 mCi. By monitoring the mitted radiation, information was obtained as to a representative heart cycle.

EXAMPLE XX

The procedure set forth in Example XVIII was repeated upon another young pig except that the eluate was administered by injecting the eluate into the root of the aorta through a catheter introduced through the carotid artery and the amount of radioactivity administered was about 25 to 30 mCi per elution. The information obtained from the emitted radioactivity simulates ejection from the left ventricle of the heart.

EXAMPLE XXI

An adsorption agent comprising porous polystyrene beads and zinc sulphide is prepared.

About 10 g of prepurified macroreticular polystyrene beads (20–50 mesh) sold under the trademark Bio-Beads SM-2 (Bio-Rad Laboratories Product) are dried by extraction with petroleum ether and ethanol, slurried in about 50 ml of a 5% solution of zinc acetate in 60% (v/v) acetic acid and then the slurry is outgassed under vacuum. After filtering the slurry, the still moist beads are added in small portions to an excess of a saturated solution of hydrogen sulphide in about 500 ml water while the solution is being stirred and hydrogen sulphide passed therethrough. After stirring for another 10 minutes, the slurry is decanted and washed several times with warm water. The polystyrene beads are then treated once again in the same manner with a solution of hydrogen sulphide in water. After washing with water and then filtering, the resulting wet cake of adsorption agent is again slurried in about 200 ml of water and the slurry boiled for about 15 minutes to remove the last traces of hydrogen sulphide. After cooling, washing with water and filtering, the adsorption agent is slurried in a small excess of water and stored under water. The adsorption agent obtained contains about 10 mg ZnS per gram of dry matter as determined by complexometric titration.

EXAMPLE XXII

A $^{195m}$Au-containing liquid is generated.

A generator is prepared according to the procedure of Example X except that an adsorption agent prepared according to Example XXI is used. The generator is charged with about 9.6 mCi of $^{195m}$Hg and eluted in the manner of Example X.

The following values are obtained upon repeated elution:

| Elution day | Elution number | Y (%) | RN (%) |
| --- | --- | --- | --- |
| 2 | 1 | 18.5 | 0.02 |
| | 2 | 22.1 | 0.006 |
| | 3 | 23.9 | 0.007 |
| | 4 | 23.0 | 0.008 |
| | 5 | 24.8 | 0.01 |
| | 6 | 23.8 | 0.008 |
| 3 | 1 | 23.0 | 0.01 |
| | 2 | 23.8 | 0.001 |
| | 3 | 22.8 | 0.007 |
| | 4 | 26.4 | 0.008 |
| 4 | 1 | 24.5 | 0.02 |
| | 2 | 23.5 | 0.009 |
| | 3 | 23.9 | 0.005 |
| | 4 | 25.0 | 0.005 |
| | 5 | 23.6 | 0.007 |
| | 6 | 23.4 | 0.005 |

EXAMPLE XXIII

Use of $^{195m}$Au for Serial First Pass Radionuclide Angiocardiography During Upright Exercise First pass radionuclide angiocardiography studies with $^{195m}$Au were made on 15 patients with coronary artery disease when the patients were at rest, at the end of several 3-minute stages of exercise, and immediately post-exercise. The exercise was performed on an upright bicycle ergometer. The patient pedalled at a constant speed beginning with a load of 150 kpm/min.; each 3 minutes, the load was increased by 150 kpm/min. $^{195m}$Hg/$^{195m}$Au generators, as described in this application, were used in this study.

Before being used in patients, quality control and analysis of performance of each individual generator were performed. First, the generator was flushed at least 10 times with 2 ml of eluent to wash off the $^{195m}$Hg and $^{195}$Hg freed from the column by radioautolysis. Subsequently, the eluate (2 ml) was measured in a standard dose calibrator (Model CRC-17, Capintec, Montvale, NJ) to determine the amount of $^{195m}$Au obtained and the breakthrough of $^{195m}$Hg. Absolute calibration was performed using a standard reference source of selenium-75. Dose calibrator readings for $^{195m}$Hg and $^{195m}$Au were corrected based upon these absolute calibrations. Before the beginning of a patient study, the activity of $^{195m}$Au in the eluate was measured 15 seconds after the time of the beginning of elution. This was representative of the approximate time following elution at which the radioactive bolus was to be injected. At 15 minutes after elution, the amount of $^{195m}$Hg breakthrough in the eluate also was measured. Estimated human radiation doses were calculated based on bio-distribution studies of $^{195m}$Hg and its descendents $^{195m}$Au, $^{195}$Hg and $^{195}$Au in animals at 48 hours after injection.

The five generators used for the present study contained 168±25 mCi of $^{195m}$Hg on the day of use. The activity of $^{195m}$Au obtained at 15 seconds after elution of these five generators ranged from 35 mCi to 16 mCi (mean 22±8 mCi). The yield of $^{195m}$Au at the time of elution was 39±6 percent (expressed as percent of $^{195m}$Au activity on the generator). The $^{195m}$Hg breakthrough per 2 ml of eluate ranged from 50µCi to 5µCi (mean 32±12 µCi). Therefore, in order not to exceed a dose of 5 rads to the kidney, or a total of 295 µCi of $^{195m}$Hg (as recommended by the FDA), the total number of sequential injections permitted per patient ranged 6 to 15 (mean 10±4).

First-pass radionuclide angiocardiography was performed with a computerized multi-crystal scintillation camera (Baird-Atomic System-77, Bedford, MA). The method for firt-pass radionuclide angiocardiography employed had been standardized and validated using $^{99m}$Tc. All patients had an 18-gauge, 1½-inch polyethylene catheter placed in a large antecubital vein for radionuclide injection. Subsequently, the lead-shielded $^{195m}$Hg/$^{195m}$Au generator was placed approximately 12 inches from the patient's injection site and adjacent to the crystal surface of the gamma camera to minimize scatter emanating from the generator. At least 15 minutes were allowed to pass between catheter placement and the first radionuclide injection in order to minimize the effect of increased sympathetic tone associated with venepuncture and pre-study anxiety. After a period of appoximately 20 minutes, the $^{195m}$Au generator was eluted 5 times to wash off the excess of $^{195m}$Hg, $^{195}$Hg and $^{195}$Au. Subsequently, 2 resting studies separated by 2 minutes were performed using $^{195m}$Au. These resting studies were performed with the patient sitting in an upright position on the bicyle ergometer. The patient was oriented in the anterior position with the detector of the multi-crystal camera vertical and directly in front of the chest. The feet were placed on the bicycle's pedals in a position identical to that employed during the subsequent exercise study.

For the first-pass studies using $^{195m}$Au, the generator was flushed rapidly with 2 ml of eluent while the eluate was withdrawn simultaneously from the outlet of the column. The eluate then was introduced into a 3 ml extension tube filled with normal saline and connected to the catheter in the antecubital vein. Subsequently, first-pass radionuclide angiocardiography was performed in the anterior position by flushing the dose as rapidly as possible with 20 cc of normal saline contained in a separate syringe attached to the extension tube by a 3-way stopcock. The time interval between elution of the generator and rapid injection was approximately 7–10 seconds. During exercise, first-pass angiocardiography was repeated during the last 15 seconds of each threeminute exercise stage. Within less than one minute of the termination of exercise, an additional first-pass study was performed. This latter study was obtained with the patient pedaling slowly against no resistance.

The scintillation data obtained of the transit of the bolus through the central circulation were recorded at 50 msec/frame for the resting studies and at 25 msec/frame for the exercise studies and stored in computer memory. The pulse height analyzer settings of the multicrystal were adjusted for the photon energy of the radiotracer used. For the 262 keV photons from $^{195m}$Au, the settings were window 50, bias 8 and lower level 20; for the 140 keV photons from $^{99m}$Tc, the settings were window 30, bias 6 and lower level 10. Field uniformity correction for studies with $^{195m}$Au was performed using a flood source containing mercury203 ($^{203}$Hg) (279 keV). For studies with $^{99m}$Tc, a cobalt-57 ($^{57}$Co) flood source (123 keV) was employed. For processing of the first-pass studies using $^{195m}$Au, the data were corrected for the decay of a radionuclide. Subsequent processing was performed as described previously. A background corrected time-activity-curve (summed representative cycle) was generated from an area of interest over the left ventricle. Left ventricular ejection fraction then was calculated in the conventional manner: end-diastolic counts minus end-systolic counts divided by end-diastolic counts.

Figure 3:
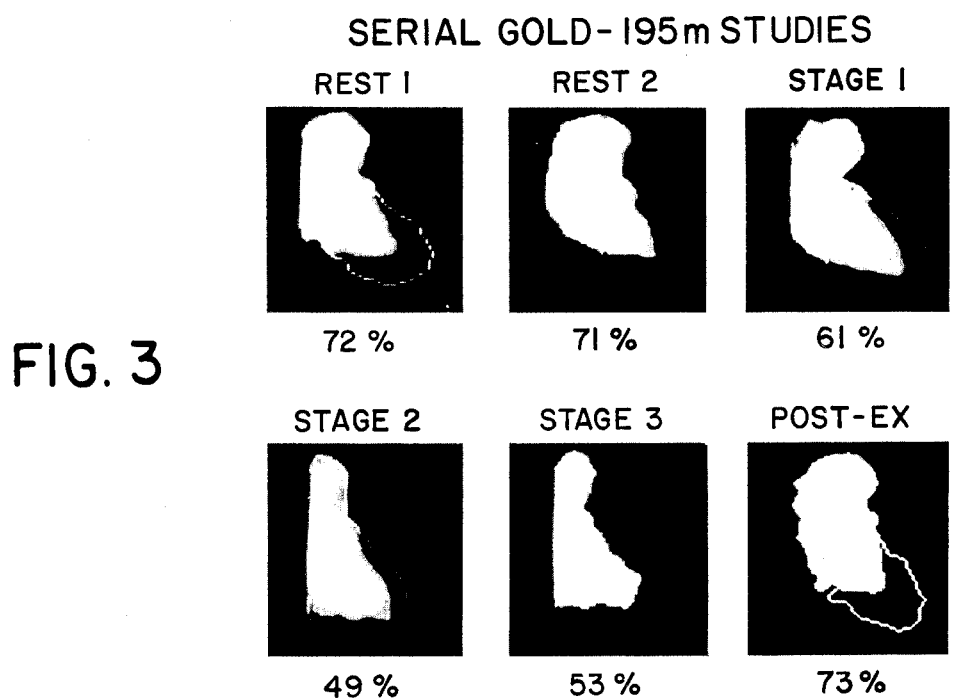
FIG. 3 represents photographs of serial first pass radionuclide angiocardiography with $^{195m}$Au in a patient.

FIG. 3 represents six photographs taken of serial first pass radionuclide angiocardiography with $^{195m}$Au in one of the patients. In each figure, the end systolic images are superimposed over the end diastolic perimeter. The photographs were taken with the patient at rest, at the end of each of three stages of exercise, and within 1 minute of termination of exercise. Displayed below each image is the calculated left ventricular ejection fraction. Left ventricular ejection fraction decreased progressively during exercise, then returned to baseline value within one minute after termination of exercise.

EXAMPLE XXIV

Combined Myocardial Perfusion

The efficiency of performing combined myocardial perfusion and left ventricular function studies in a single test was evaluated with four of the patients of Example XXIII above. Two mCi of $^{201}$Tl was injected in the intravenous line approximately 1 minute before termination of the bicycle exercise. After completion of the $^{195m}$Au first-pass studies as described above, myocardial imaging was begun within less than 5 minutes of the end of exercise. Imaging was performed using a single crystal gamma camera (General Electric 400T, Milwaukee, Wisc.) equipped with an all purpose parallel-hole collimator interfaced with a dedicated microcomputer (STAR, General Electric, Milwaukee, Wisc.). Images were obtained for a pre-set time (10 minutes) in the anterior, left-anterior-oblique and left lateral positions. Delayed imaging was performed for identical time per view as for the immediate post-exercise study 3–4 hours after the initial study. Background subtracted images were displayed on white and black Polaroid film and were analyzed qualitatively by visual inspection.

Figure 4:
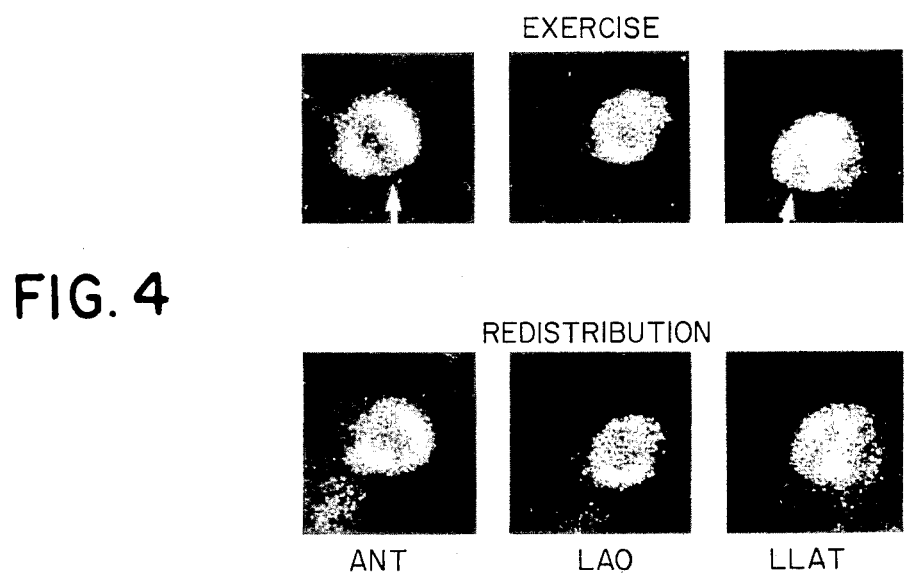
FIG. 4 represents several images of 201Tl scintigraphy in a patient who previously had undergone first pass radionuclide angiocardiography.

The multiple $^{195m}$Au first-pass studies prior to myocardial imaging had no apparent effect on the quality of the $^{201}$Tl images. In all 4 patients the studies were of excellent quality and uniformly abnormal, consistent with exercise-induced myocardial ischemia and/or myocardial infarction. FIG. 4 provides six images of $^{201}$Tl scintigraphy in a patient who previously had undergone left ventricular function studies during exercise. The arrow superimposed over the images shows an inferoapical perfusion defect present immediately after exercise which fills in at delayed imaging (redistribution). The patient had a total of seven first pass studies with $^{195m}$Au during the same exercise test. The $^{201}$Tl was injected during the second minute of stage 3 when the patient experienced angina pectoris. Shortly thereafter, two additional first pass studies were performed with $^{195m}$Au at peak exercise and during the immediate post exercise recovery period before $^{201}$Tl myocardial imaging was started. In FIG. 4, ANT, LAO, and LLAT represent anterior, left anterior oblique and left lateral, respectively.

EXAMPLE XXV $^{195m}$Au Studies on Pulmonary Circulation $^{195m}$Au was used to study rapid changes in pulmonary circulation induced by exercise in normal subjects and patients with coronary heart disease and exercise induced asthma. Tests were conducted to measure regional changes in blood volume and flow and so provide information about recruitment of vascular beds during exercise.

Six healthy people (the control group), seven patients with coronary heart disease and five patients with exercise induced asthma were studied at rest in the sitting position and during maximum exercise.

The exercise test was performed by having each subject sit on an electrically braked bicycle ergometer with workload increments of 10W/min. Exercise was stopped because of general fatigue or breathlessness; in all of the coronary heart disease patients, angina was provoked.

21.6–32.4 mCi of $^{195m}$Au were injected with the subjects at rest, at maximum work-load and four minutes after exercise. Additional injections were made in the patients with exercise induced asthma ten minutes after exercise and after administration of terbutaline aerosol. Injections were made through a short catheter placed in a medial cubital vein. The catheter was connected on-line to a $^{195m}$Au-generator. All injections were made during reactive hyperemia which was produced by inflating a blood-pressure cuff proximal to the injections site to supra-systolic pressure for 2–3 minutes prior to injection.

The first-pass of the isotope through the central circulation was recorded in the posterior view with a gamma camera (GE 400T) equipped with a high energy collimator; 0.1 sec frames were collected for 20 seconds and stored in digitalized form on magnetic discs in a computer (PDP-11).

A transmission scan was obtained using a $\phi\beta$Co flood-source in order to define the outline of the lung. Transmissions scanning was performed immediately prior to or after each injection of $^{195m}$Au.

Regional distribution of lung activity was studied in images representing the time interval when practically all activity was present in the lung fields, with little or no activity in the heart. A redistribution of activity toward the lung apex was found during exercise, and the change was found to be more pronounced in the control group than in the patients with coronary heart disease. In two of the three patients in which exercise induced asthmatic attack, gross reductons in the activity was seen in different areas of the lung.

The regional distribution of lung activity was analyzed in two ways. In the control and in the patients with coronary heart disease activity profiles representing apicobasal distribution of activity were generated from a vertical region of interest (ROI), approximately 3 cm wide, placed over the middle of the right lung. Apical and basal lung boundaries were defined from the transmission scan. Activity profiles in a healthy control at rest and at maximum exercise were drawn up. Activity on the X-axis was presented as percent of total counts in the region of interest. Lung boundaries were defined from the transmission scan. Straight lines indicated the fit made by hand to define the downscope of the curves. The ratio of the slope of the straight line at rest and one obtained during exercise was used as an index of the redistribution of activity in the lungs.

In the patients with exercise induced asthma changes in the distribution of activity between the lungs was estimated from activity in two symmetrical ROIs. The distribution was expressed in percent as: 100 ×(Right)/(Right+Left). Time activity curves were generated from a large ROI over the right lung. The peak of the curve was almost symmetrical, and the full width of this peak at half maximum was taken as a measure of the pulmonary transit time.

While the present invention has been described with reference to particular embodiments thereof, it will be understood that numerous modifications may be made without departing from the spirit and scope of the invention.

I claim:

1. A process for performing a radiodiagnostic examination in a living being comprising administering to the living being a non-toxic, pharmaceutically acceptable $^{195m}$Au-containing liquid which is produced by
   (a) adsorbing $^{195m}$Hg on a chemically and radiolytically stable adsorption agent comprising a mercury ion binding material having a significantly higher affinity for mercury ions than for gold ions, and
   (b) eluting the daughter $^{195m}$Au radioisotope with an eluant which selectively converts $^{195m}$Au ions to an elutable form in the presence of the adsorbed parent $^{195m}$Hg radioisotope, and which is non-toxic and pharmaceutically acceptable, and monitoring the radioactivity emitted from the living being.

2. A process in accordance with claim 1 wherein the adsorption agent used in the production of the $^{195m}$Au-containing liquid is selected from the group consisting of activated carbon, silver, hydrated manganese dioxide, and metal sulfides and said eluant is a nontoxic, pharmaceutically acceptable solution which selectively converts $^{195m}$Au to an elutable form.

3. A process in accordance with claim 1 wherein the adsorption agent used in the preparation of the $^{195m}$Au-containing liquid contains a substrate material selected from polymers and copolymers of styrene.

4. A process in accordance with claim 1 wherein the adsorption agent used in the production of the $^{195m}$Au-containing liquid comprises particulate substrate material and the mercury ion-binding material is on the surface of the particles of the substrate material.

5. A process in accordance with claim 4 wherein the mercury ion-binding material is chemically bonded to the surfaces of the particles of substrate material.

6. A process in accordance with claim 4 wherein the substrate material is selected from the group consisting of silica gel, silicate material and glass.

7. A process in accordance with claim 6 wherein the mercury ion-binding material is chemically bonded to the surfaces of the particles of substrate material.

8. A process in accordance with claim 5 wherein the mercury ion-binding material has a terminal functional group selected from the group consisting of thiol-, amino-, hydroxy-, carbonate-, dithiocarbonate-, xanthate-, and carboxy- functional groups.

9. A process in accordance with claim 7 wherein the mercury ion-binding material has a terminal functional group selected from the group consisting of thiol-, amino, hydroxy-, carbamate-, dithiocarbamate-, xanthate-, and carboxy-functional groups.

10. A process in accordance with claim 4 wherein the adsorption agent for the parent isotope $^{195m}$Hg includes particulate silica gel, the particles of which have zinc sulphide at the surface, and the eluant for the daughter radioisotope is a solution of thiosulphate.

11. A process in accordance with claim 4 wherein the adsorption agent for the parent isotope includes particulate silica gel, the particles of which have hydrated manganese dioxide at the surface and the eluant for the daughter radioisotope is a solution of a gold complexing agent selected from the group consisting of tris(hydroxymethyl)aminomethane and hippurate.

12. A process in accordance with claim 4 wherein the adsorption agent for the parent isotope includes particulate silica gel, the particles of which have silver sulphide at the surface, and the eluant for the daughter radioisotope is a solution of a gold-complexing agent selected from the group consisting of glutathione and thiomalate.

13. A process for performing a radiodiagnostic examination in a living being comprising administering to the living being a non-toxic, pharmaceutically acceptable $^{195m}$Au-containing liquid which is produced by a radioisotope generator system which comprises
   (a) a chemically and radiolytically stable mercury ion-binding adsorption agent having a significantly higher affinity for mercury ions than for gold ions;
   (b) $^{195m}$Hg adsorbed on said adsorption agent as a parent radioisotope; and
   (c) an eluant for eluting said daughter radioisotope which selectively converts $^{195m}$Au ions to an elutable form in the presence of the adsorbed parent $^{195m}$Hg radioisotope, is non-toxic and pharmaceutically acceptable.

* * * * *